US008823384B2

(12) United States Patent
Matsuoka et al.

(10) Patent No.: US 8,823,384 B2
(45) Date of Patent: Sep. 2, 2014

(54) FINE PARTICLE DETECTION SYSTEM

(75) Inventors: Toshiya Matsuoka, Kaizu (JP);
Masayuki Motomura, Komaki (JP);
Takeshi Sugiyama, Gifu (JP); Keisuke Tashima, Kasugai (JP); Hitoshi Yokoi, Ama (JP)

(73) Assignee: NGK Spark Plug Co., Ltd., Aichi (JP)

( * ) Notice: Subject to any disclaimer, the term of this patent is extended or adjusted under 35 U.S.C. 154(b) by 325 days.

(21) Appl. No.: 13/444,057

(22) Filed: Apr. 11, 2012

(65) Prior Publication Data
US 2012/0262182 A1 Oct. 18, 2012

(30) Foreign Application Priority Data

Apr. 12, 2011 (JP) ................................ 2011-088549

(51) Int. Cl.
*G01N 27/70* (2006.01)
*G01N 15/06* (2006.01)

(52) U.S. Cl.
CPC ........ *G01N 15/0656* (2013.01); *F01N 2560/05* (2013.01)
USPC ............................ 324/464; 324/459; 324/465

(58) Field of Classification Search
CPC .. G01N 27/62; G01N 27/70; G01N 2030/642
USPC ......................................... 324/464–470, 71.4
See application file for complete search history.

(56) References Cited

U.S. PATENT DOCUMENTS

| 3,114,877 | A | * | 12/1963 | Dunham | 324/71.1 |
| 5,153,519 | A | * | 10/1992 | Wentworth et al. | 324/464 |
| 6,246,002 | B1 | * | 6/2001 | Rumsey | 174/84 R |
| 6,906,322 | B2 | * | 6/2005 | Berggren et al. | 250/288 |
| 7,651,586 | B2 | * | 1/2010 | Moriya et al. | 156/345.47 |
| 2011/0050243 | A1 | * | 3/2011 | Tikkanen | 324/464 |
| 2011/0198511 | A1 | * | 8/2011 | Graupera et al. | 250/396 R |
| 2011/0246089 | A1 | * | 10/2011 | Barrett et al. | 702/24 |

FOREIGN PATENT DOCUMENTS

WO 2009/109688 A1 9/2009

* cited by examiner

*Primary Examiner* — Arleen M Vazquez
*Assistant Examiner* — Dominic Hawkins
(74) *Attorney, Agent, or Firm* — Sughrue Mion, PLLC

(57) ABSTRACT

There is provided a fine particle detection system with a fine particle sensor, a cable and a sensor drive control device. The fine particle sensor has an ion source unit with first and second electrodes, a particle charging unit and inner and outer sensor casings. The cable has a power supply wiring line connected to the second electrode, an inner shield line electrically continuous with the inner sensor casing and an outer shield line electrically continuous with the outer sensor casing. The sensor drive control device has an ion-source power supply circuit, a signal current detection circuit, an inner circuit casing electrically continuous with a first output terminal of the ion-source power supply circuit and surrounding the ion-source power supply circuit and an outer circuit casing connected to the ground potential and shielding the ion-source power supply circuit, the signal current detection circuit and the inner circuit casing.

8 Claims, 9 Drawing Sheets

FINE PARTICLE DETECTION SYSTEM

BACKGROUND OF THE INVENTION

The present invention relates to a fine particle detection system for detecting the amount of fine particles such as soot in exhaust gas flowing through an exhaust pipe.

Fine particles such as soot are contained in exhaust gases of internal combustion engines (e.g. diesel engines and gasoline engines). It is common practice to purify the exhaust gas by collecting the fine particles from the exhaust gas with the use of a filter. It is also feasible to heat the filter to a high temperature that the collected fine particles can be burned off from the filter.

In the event of a deterioration or defect (e.g. breakage) in the filter, the unpurified exhaust gas is directly discharged downstream of the filter. There is thus a demand for a fine particle detection system capable of detecting the amount of fine particles in exhaust gas in order to directly measure the amount of fine particles in the exhaust gas (unpurified exhaust gas) and to detect the occurrence of a deterioration or defect in the filter. International Application Publication No. WO2009/109688 discloses one type of fine particle detection system that introduces exhaust gas from an exhaust pipe, mixes the exhaust gas with ionized gas containing positive ions so as to charge fine particles in the exhaust gas by the positive ions, discharges the exhaust gas together with the charged fine particles to the exhaust pipe, and then, determines the concentration of the fine particles in the exhaust gas based on an electric current (called "signal current") flowing according to the amount of the charged fine particles discharged to the exhaust pipe.

SUMMARY OF THE INVENTION

The signal current of the fine particle detection system, which is responsive to the amount of fine particles in the exhaust gas, is very low in intensity during normal operations of the internal combustion engine. For example, the signal current of the fine particle detection system is of the order of pA in the case where the electric current supplied for generation of the ionized gas by aerial discharge (called "discharge current") is of the order of μA. That is, the signal current of the fine particle detection system is only about one-thousandth of the discharge current.

At the generation of aerial discharge, however, there may arise an error in the signal current in the occurrence of a so-called leakage current from any structural component or wiring line of the fine particle detection system. There may also arise an error in the signal current upon superimposing of external electromagnetic noises onto the passage of the discharge current or signal current in the fine particle detection system. It is thus difficult to accurately measure the fine particle amount of the exhaust gas based on the signal current under the influence of the leakage current and electromagnetic noises.

The present invention has been made in view of the above circumstances. It is accordingly an object of the present invention to provide a fine particle detection system for properly detecting a signal current responsive to the amount of fine particles in exhaust gas.

According to one aspect of the present invention, there is provided a fine particle detection system for detecting the amount of fine particles in exhaust gas flowing through a metallic exhaust pipe, comprising: a fine particle sensor mounted to the exhaust pipe; a lead extending from the fine particle sensor; and a sensor drive control device connected to the lead, the fine particle sensor comprising: an ion source unit; a particle charging unit; an inner sensor casing; and an outer sensor casing, the ion source unit having: a first electrode set to a first floating potential; and a second electrode set to a second floating potential that is a positive or negative potential having an effective potential value higher than that of the first floating potential, to generate ions by aerial discharge between the first and second electrodes, the particle charging unit having: a gas inlet hole for introducing the exhaust gas from the exhaust pipe; a mixing space for mixing the introduced exhaust gas with the ions generated from the ion source unit so as to form charged fine particles by charging the fine particles in the introduced exhaust gas with some of the ions; a gas outlet hole for discharging the introduced exhaust gas together with the charged fine particles to the exhaust pipe; and a trapping electrode being electrically continuous with the first electrode and adapted to trap a remainder of the ions that remain as stray ions without being used for charging of the fine particles, the inner sensor casing being electrically continuous with the first electrode and the particle charging unit, while being electrically insulated from the second electrode and the exhaust pipe, and located at a position nearer to the lead than the ion source unit and the particle charging unit so as to circumferentially surround the second electrode, the outer sensor casing being electrically continuous with the exhaust pipe and thereby set to a ground potential, while being electrically insulated from the second electrode, the particle charging unit and the inner sensor casing, and located so as to circumferentially surround and electromagnetically shield parts of the ion source unit, the particle charging unit and the inner sensor casing located outside the exhaust pipe, the lead being a double-shield cable having: a power supply wiring line connected to the second electrode; an inner shield line being electrically continuous with the inner sensor casing, while being electrically insulated from the power supply wiring line, and circumferentially surrounding the power supply wiring line; and an outer shield line being electrically continuous with the outer sensor casing, while being electrically insulated from the inner shield line, and circumferentially surrounding and electromagnetically shield the inner shield line, the sensor drive control device comprising: an ion-source power supply circuit; a signal current detection circuit; an inner circuit casing; and an outer circuit casing, the ion-source power supply circuit having: a first output terminal set to the first floating potential and being electrically continuous with the first electrode of the ion source unit through the inner shield line; and a second output terminal being electrically continuous with the second electrode of the ion source unit through the power supply wiring line, and adapted to output a predetermined constant current through the second output terminal, the current signal detection circuit having: a signal input terminal connected to the first output terminal of the ion-source power supply circuit; and a ground input terminal connected to the ground potential, to detect a signal current flowing between the first output terminal of the ion-source power supply circuit and the ground potential, the inner circuit casing being electrically continuous with the first output terminal of the ion-source power supply circuit and surrounding the ion-source power supply circuit, the outer circuit casing connected to the ground potential and surrounding and electromagnetically shielding the ion-source power supply circuit, the inner circuit casing and the current signal detection circuit.

The other objects and features of the present invention will also become understood from the following description.

and a sensor drive control device according to one exemplary embodiment of the present invention.

Figure 2:
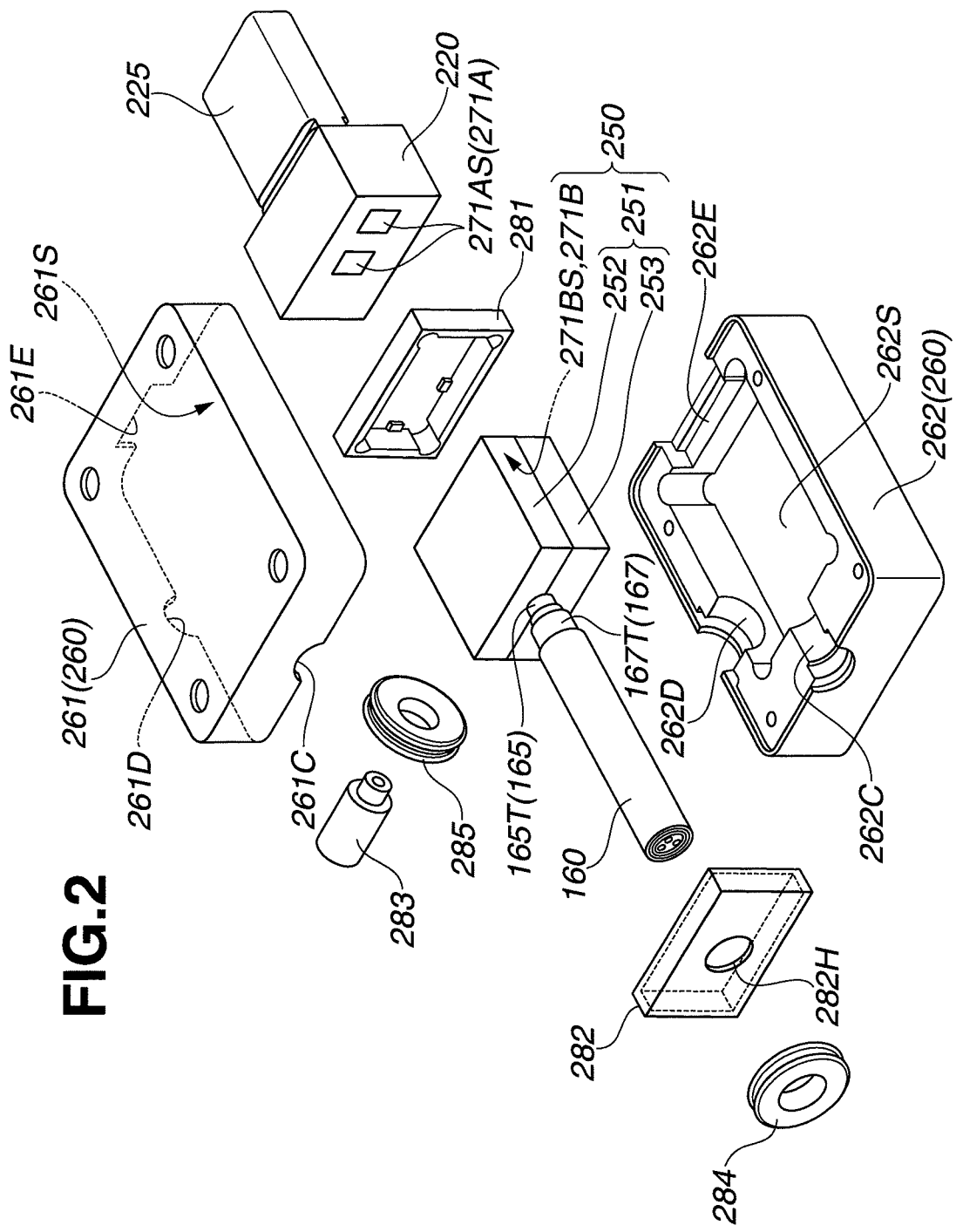

FIG. 2 is an exploded perspective view of a sensor control circuit unit of the sensor drive control device according to the exemplary embodiment of the present invention.

Figure 3:
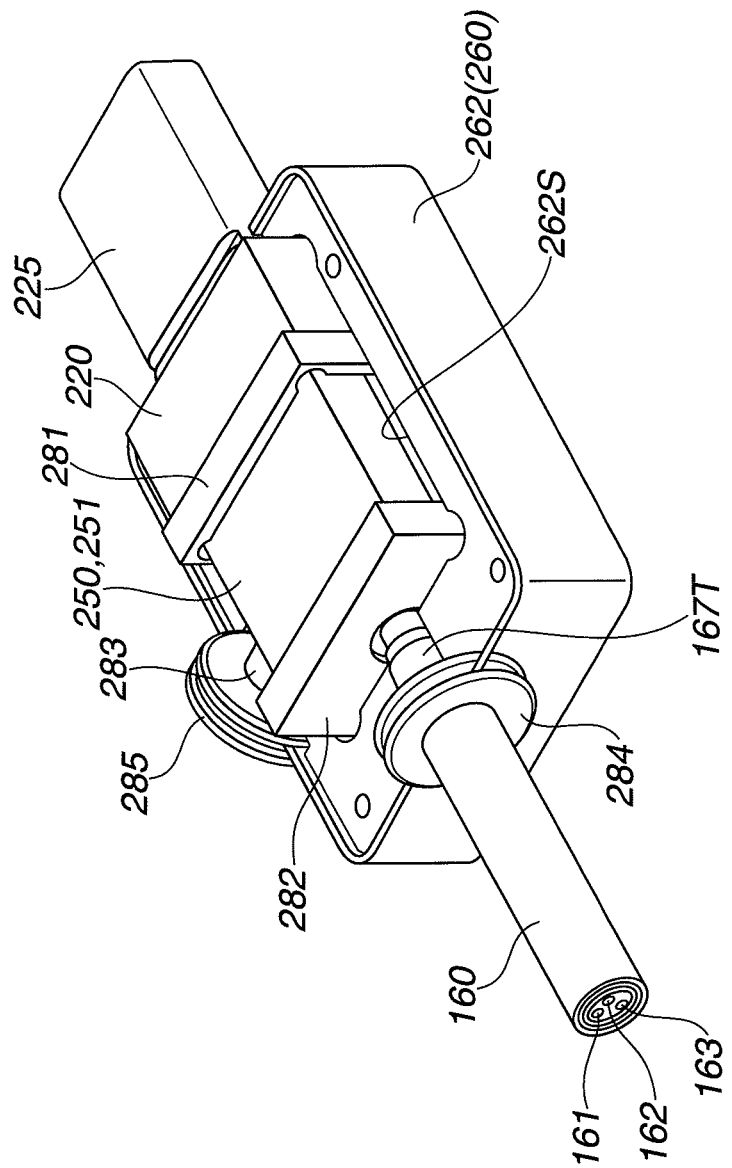
Figure 4:
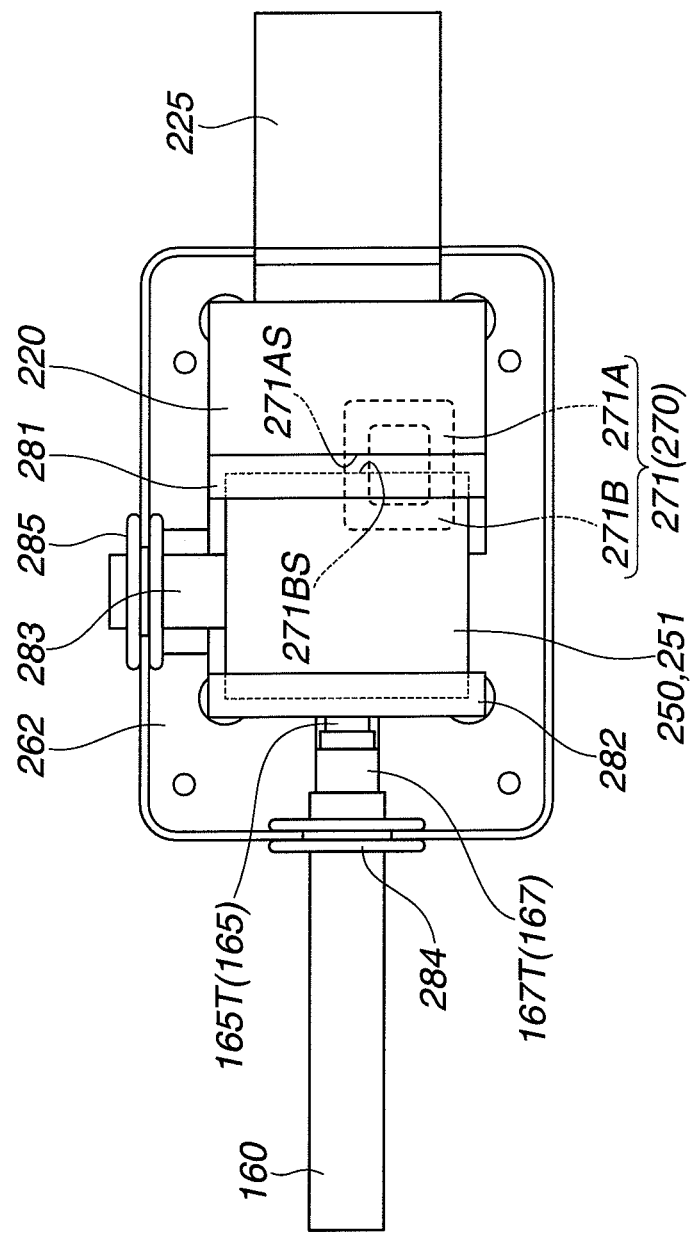

FIGS. 3 and 4 are a perspective view and a plan view of the sensor control circuit unit, in a state that a first outer case member is detached from the sensor control circuit unit, according to the exemplary embodiment of the present invention.

Figure 5:
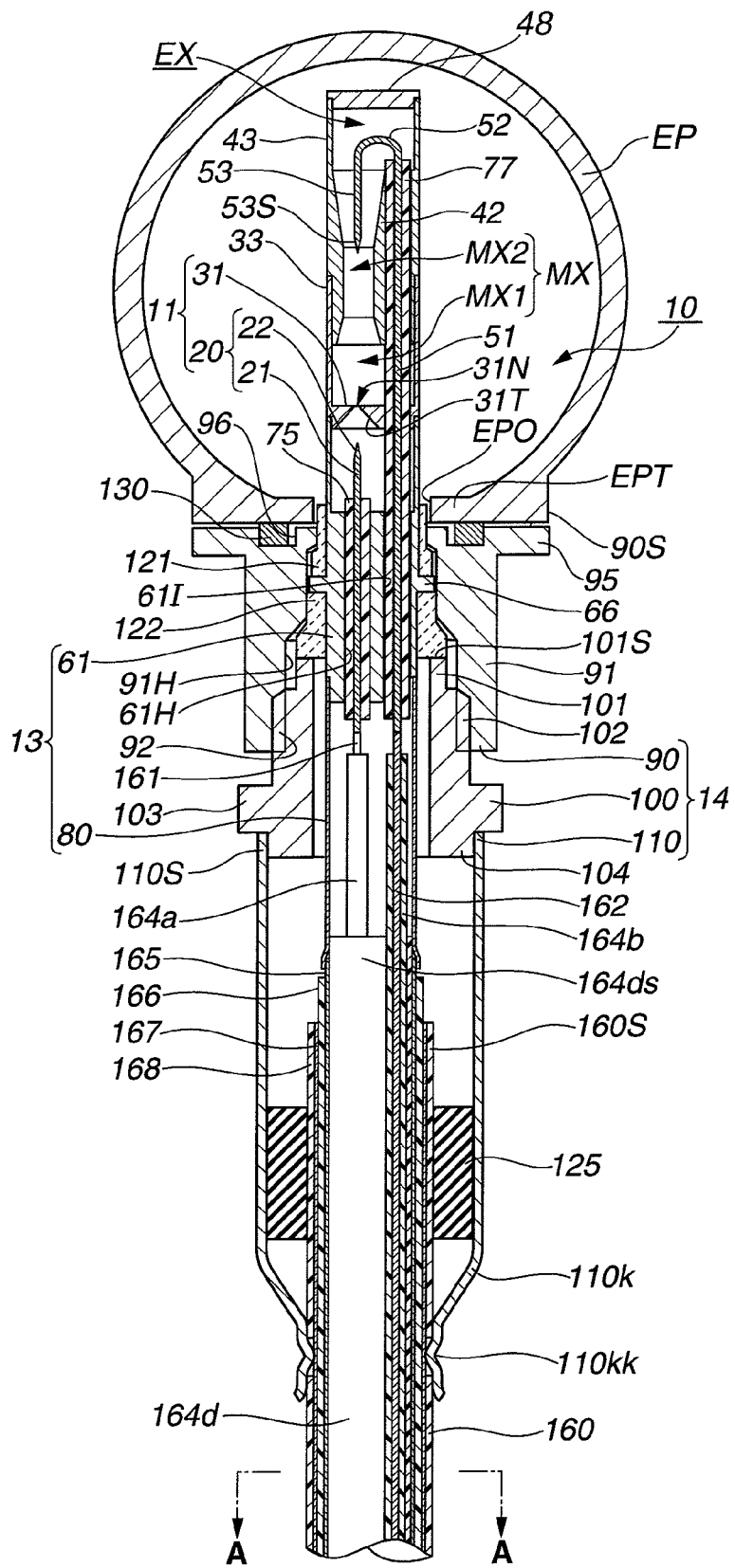
Figure 6:
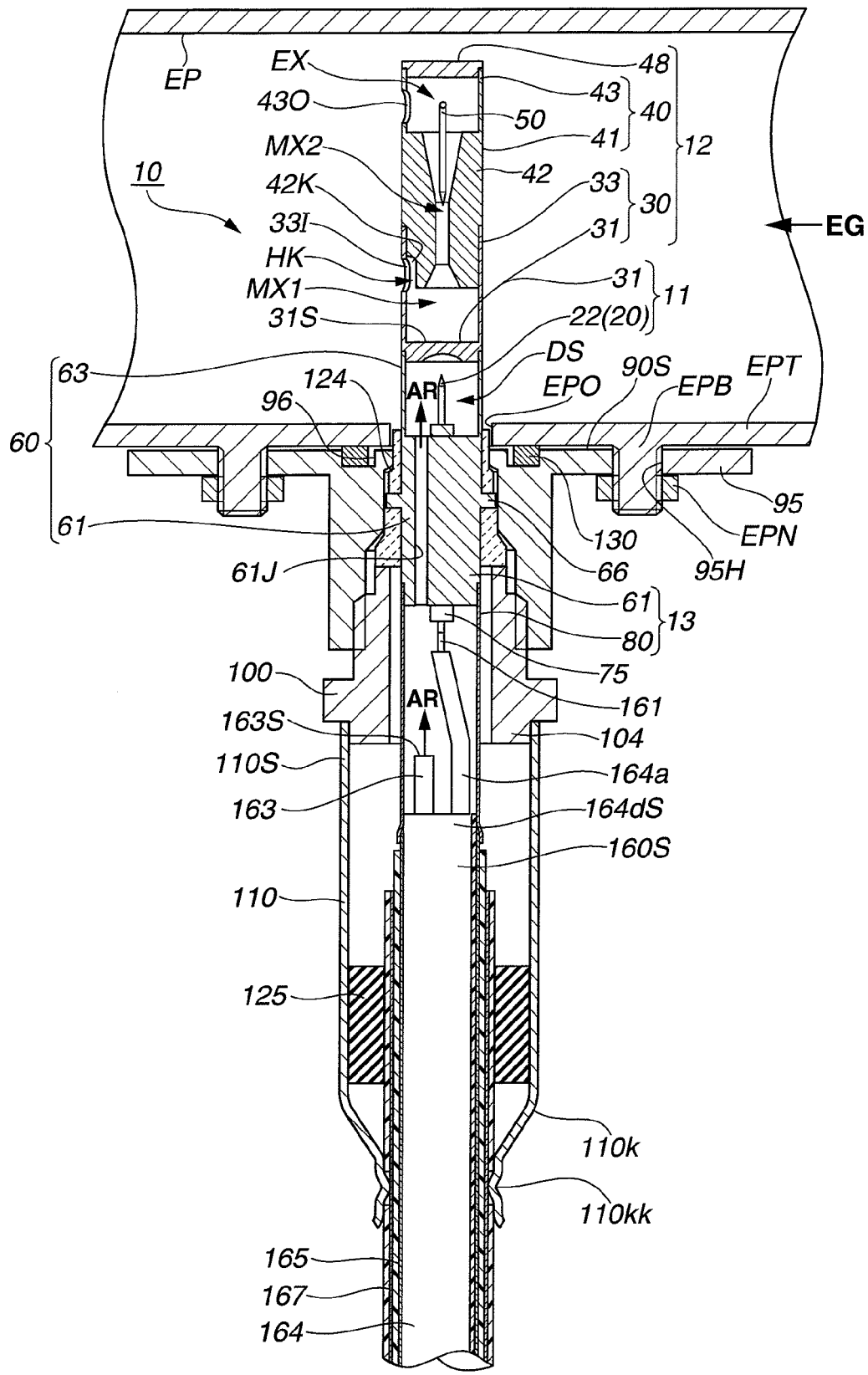

FIGS. 5 and 6 are vertical section views of the fine particle sensor, taken in perpendicular directions, according to the exemplary embodiment of the present invention.

Figure 7:
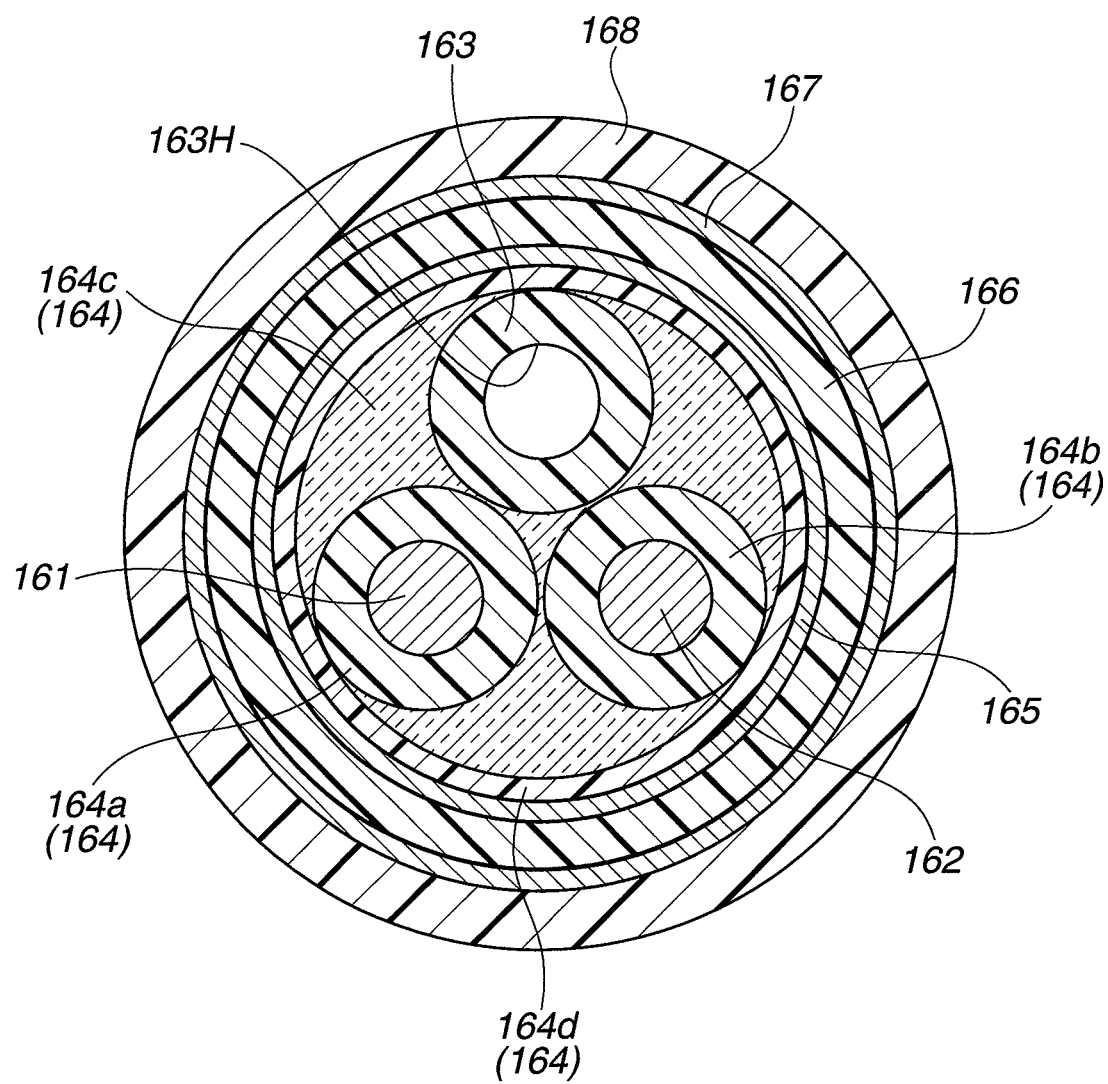

FIG. 7 is a lateral section view of the cable, taken in a direction of line A-A of FIG. 5, according to the exemplary embodiment of the present invention.

Figure 8:
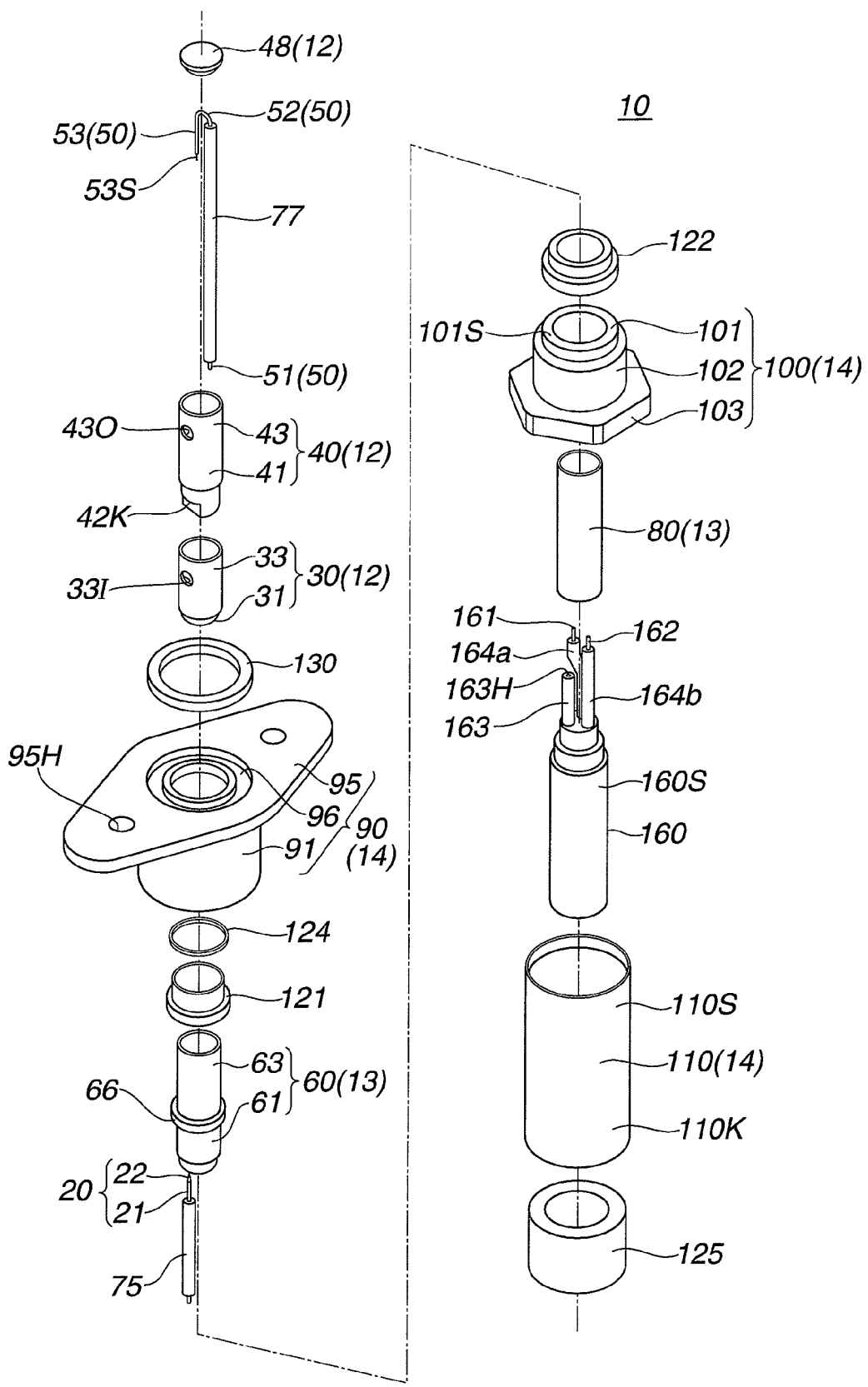

FIG. 8 is an exploded perspective view of the fine particle sensor according to the exemplary embodiment of the present invention.

Figure 9:
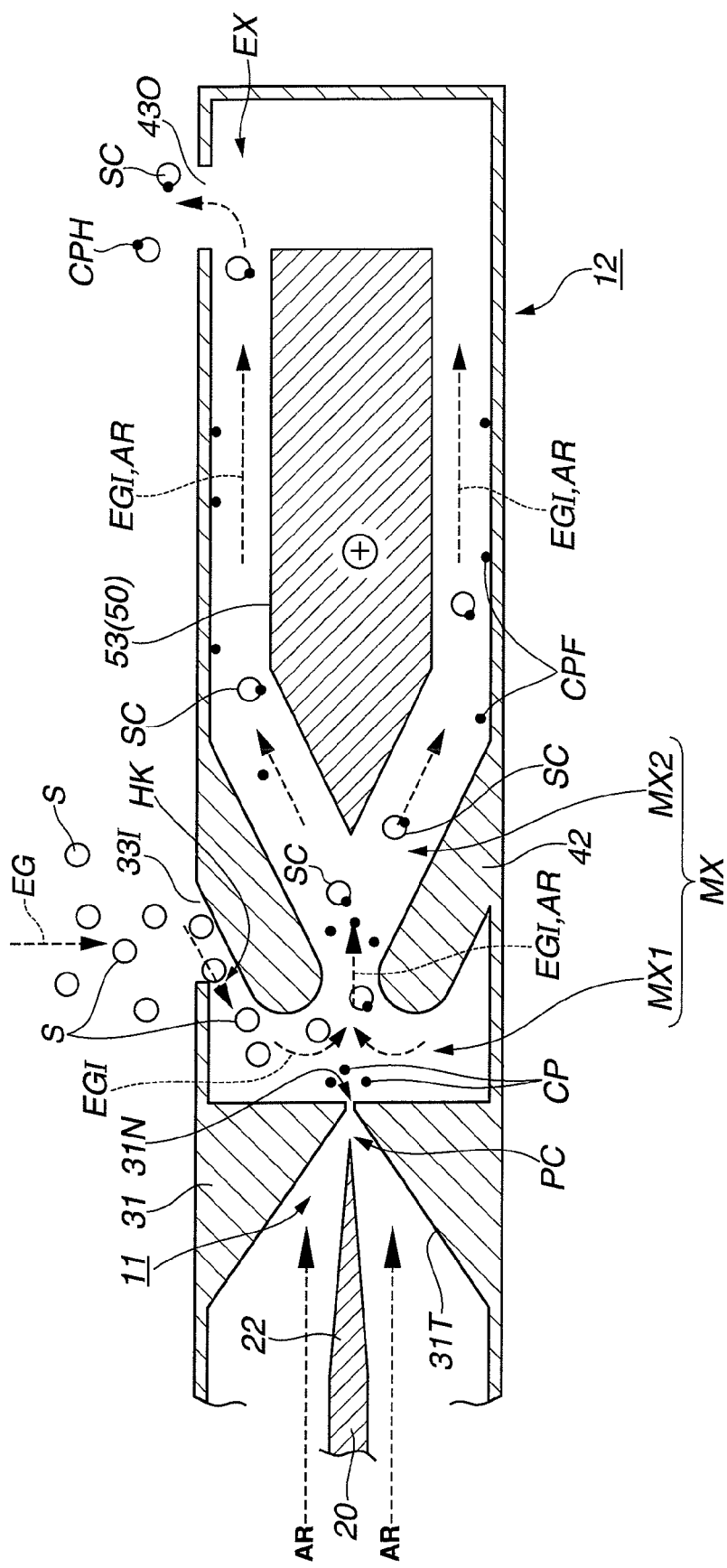

FIG. 9 is a schematic view showing the flow of fine particles in a particle charging unit of the fine particle sensor according to the exemplary embodiment of the present invention.

DESCRIPTION OF THE EMBODIMENTS

The present invention will be described below in detail with reference to the drawings.

Figure 1:
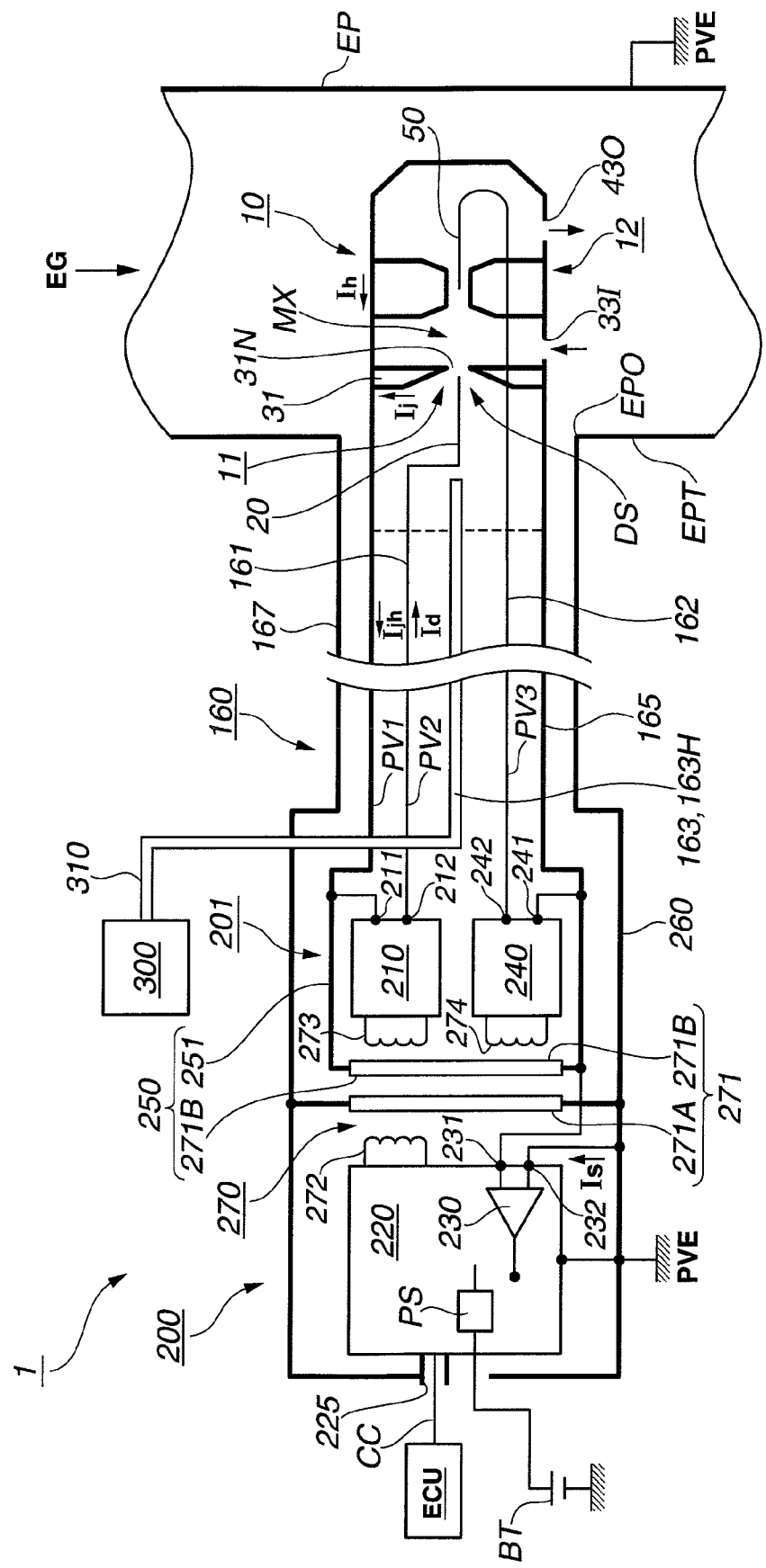
FIG. 1 is a schematic block diagram of a fine particle detection system with a fine particle sensor, a cable (as a lead)

Referring to FIG. 1, the following embodiment of the present invention refers to a fine particle detection system 1 for detecting the amount of fine particles in exhaust gas EG flowing through a metallic exhaust pipe EP of an internal combustion engine in a vehicle. The fine particle detection system 1 generally includes a fine particle sensor 10 mounted by insertion into a sensor mounting portion EPT of the exhaust pipe EP, a cable 160 extending from the fine particle sensor 10, a sensor drive control device 200 connected to the cable 160 and a transfer pump 300 connected to the cable 160.

It is herein noted that: in the following description, the terms "front" and "rear" are used with respect to the direction of insertion of the fine particle sensor 10 into the exhaust pipe EP; and some of the drawings are simplified by e.g. omitting the circuit wiring or illustrating the circuit components in block form.

As shown in FIG. 1, the sensor drive control device 200 has a sensor control circuit unit 201 that drives the fine particle sensor 10 through the cable 160, receives a signal current Is of the fine particle sensor 10 through the cable 160 and determines the fine particle amount of the exhaust gas EG according to the signal current Is of the fine particle sensor 10. The sensor control circuit unit 201 includes an ion-source power supply circuit 210, an auxiliary-electrode power supply circuit 240, a measurement circuit module 220, an isolation transformer 270, an inner circuit casing 250 and an outer circuit casing 260.

The ion-source power supply circuit 210 has a first output terminal 211 set to a first floating potential PV1 and a second output terminal 212 set to a second floating potential PV2. The second floating potential PV2 is a positive potential higher than the first floating potential PV1 in the present embodiment. For example, the second floating potential PV2 is set to a positive pulse voltage having a peak value of 1 to 2 kV, by half-wave rectification of a sine wave of the order of 100 kHz, relative to the first floating potential PV1.

In the present embodiment, the ion-source power supply circuit 210 is in the form of a constant-current supply circuit that performs feedback control on its output current and maintains the effective value of the output current autonomously at a predetermined constant value of the order of several µA (e.g. 5 µA).

The auxiliary-electrode power supply circuit 240 has a first output terminal 241 set to the first floating potential PV1 and a second output terminal 242 set to a third floating potential PV3. The third floating potential PV3 is a positive direct-current potential higher than the first floating potential PV1 but lower than the peak value of the second floating potential PV2 in the present embodiment. For example, the third floating potential PV3 is set to a DC voltage of 100 to 200 V.

The measurement circuit module 220 includes a signal current detection circuit 230 mounted on a substrate to detect the signal current Is of the fine particle sensor 10.

The signal current detection circuit 230 has a signal input terminal 231 connected to the first output terminal 211 of the ion-source power supply circuit 210 (the first floating potential PV1) and a ground input terminal 232 connected to a ground potential PVE.

The measurement circuit module 220 also includes a connector 225 and a microprocessor connected to a cable CC through the connector 225 for communication with an engine control unit ECU so as to transmit the detection result of the signal current detection circuit 230 (i.e. the intensity of the signal current Is) to the engine control unit ECU, or process the detection result of the signal current detection circuit 230 into a signal indicating the fine particle amount or indicating whether the fine particle amount exceeds a given level or not etc., and then, transmit the processing result to the engine control unit ECU.

The measurement circuit module 22 further includes a built-in regulator power supply PS connected to and driven by an external battery BT through the connector 225.

The isolation transformer 270 is arranged between the measurement circuit module 220 and the power supply circuits 210 and 240 and adapted to divide a part of power supplied to the measurement circuit module 220 through the regulator power supply PS into the power supply circuits 210 and 240. Namely, the isolation transformer 270 has the function of supplying power to not only the ion-source power supply circuit 210 but also the auxiliary-electrode power supply circuit 240.

The isolation transformer 270 can be of any known type. In the present embodiment, the isolation transformer 270 has a core assembly 271 with separable primary and secondary cores 271A and 271B, a primary coil 272 wound around the primary core 271A and secondary coils 273 and 274 wound around the secondary core 271B as shown in FIG. 1.

The primary and secondary cores 271A and 271B are slightly spaced apart and electrically insulated from each other, but allow a common magnetic flux to pass therethrough so as to accomplish the transformer function of the isolation transformer 270.

The primary coil 272 is incorporated in the measurement circuit module 220 so as to serve as a structural component of the measurement circuit module 220. The secondary coils 273 and 274 are incorporated in the power supply circuits 210 and 240 so as to serve as structural components of the power supply circuits 210 and 240, respectively. Further, the primary coil 272, the secondary coils 273 and 274 and the coil assembly 271 (the primary and secondary coils 271A and 271B) are electrically insulated from one another. The power supply circuits 210 and 240 can be thus supplied with power from the measurement circuit module 220 through the isolation transformer 270 while being kept insulated from the measurement circuit module 220.

In the isolation transformer 270, the primary core 271A is connected to the ground potential PVE; and the secondary core 271B is connected to the first output terminal 211 of the ion-source power supply circuit 210 (the first floating potential PV1).

The inner circuit casing 250 surrounds a substrate on which the ion-source power supply circuit 210 and the auxiliary-electrode power supply circuit 240 are mounted. As the first output terminal 211 of the ion-source power supply circuit 210, the first output terminal 241 of the auxiliary-electrode power supply circuit 240, the signal input terminal 231 of the signal current detection circuit 230 and the secondary core 271B of the isolation transformer 270 are electrically continuous with the inner circuit casing 250, the inner circuit casing 250 is set to the first floating potential PV1. By this inner circuit casing 250, the ion-source power supply circuit 210 and the auxiliary-electrode power supply circuit 240 are electromagnetically shielded.

Preferably, the inner circuit casing 250 is in the form of a container case 251 (hereinafter referred to as "inner circuit case") having electrical conductivity and accommodating and surrounding therein the power supply circuits 210 and 240 so as to prevent current leakage from the power supply circuits 210 and 240. It is feasible to form the inner circuit case 251 by cutting a metal material (e.g. copper, aluminum etc.) into a box shape or by shaping a metal plate (e.g. copper plate, aluminum plate), a punching metal plate, a metal wire woven net or a conductive coated plastic plate (i.e. plastic plate having a surface coated with a conductive coating layer of copper, aluminum etc.) into a box shape.

As shown in FIGS. 2 to 4, the inner circuit case 251 has substantially rectangular parallelepiped first and second inner case members 252 and 253 formed by e.g. cutting of aluminum in the present embodiment. The first and second inner case members 252 and 253 are electrically and hermetically joined together in such a manner that hollow recessed spaces of the first and second inner case members 252 and 253 face each other to accommodate therein the ion-source power supply circuit 210 and the auxiliary-electrode power supply circuit 240.

In the present embodiment, the secondary core 271B and the secondary coils 273 and 274 of the isolation transformer 270 are also accommodated in the inner circuit case 251 with a surface 271 BS of the secondary core 271B being exposed through a lateral surface of the inner circuit case 251 and facing and spaced apart from a surface 271AS of the primary core 271A as indicated by a broken line in FIG. 4. It is thus understood that the inner circuit case 251 constitutes, together with the secondary core 271B, the inner circuit casing 250 in the present embodiment.

The outer circuit casing 260 surrounds the inner circuit casing 250 in which the ion-source power supply circuit 210 and the auxiliary-electrode power supply circuit 240 are accommodated, the measurement circuit module 220 (signal current detection circuit 230) and the isolation transformer 270. Further, the outer circuit casing 260 is fixed to a chassis of the vehicle by a fixing member and thereby connected to the ground potential PVE. By this outer circuit casing 260, the ion-source power supply circuit 210, the auxiliary-electrode power supply circuit 240, the measurement circuit module 220 (signal current detection circuit 230) and the isolation transformer 270 are electromagnetically shielded. As the outer circuit casing 260 is electrically continuous with the ground input electrode 232 of the signal current detection circuit 230 and the primary core 271A of the isolation transformer 270, the ground input electrode 232 of the signal current detection circuit 230 and the primary core 271A of the isolation transformer 270 are connected to the ground potential PVE through the outer circuit casing 260.

Preferably, the outer circuit casing 260 is formed as a container case. As a material of the outer circuit casing 260, there can suitably be used those capable of preventing the entry of external electromagnetic noises into the power supply circuit 210, 240, the signal current detection circuit 230 and the isolation transformer 270. It is feasible to form the outer circuit casing 260 by cutting a metal material (e.g. copper, aluminum etc.) into a box shape or by shaping a metal plate (e.g. copper plate, aluminum plate), a punching metal plate, a metal wire woven net or a conductive coated plastic plate (i.e. plastic plate having a surface coated with a conductive coating layer of copper, aluminum etc.) into a box shape.

As shown in FIGS. 2 to 4, the outer circuit casing 260 has substantially rectangular parallelepiped first and second outer case member 261 and 262 formed by e.g. cutting of aluminum in the present embodiment. A substantially rectangular hollow recessed accommodation space 261S, 262S is formed in the center of the outer case member 261, 262. Further, a substantially semi-cylindrical cable insertion groove 261C, 262C, a substantially semi-cylindrical joint insertion groove 261D, 262D and a substantially rectangular connector installation groove 261E, 262E are formed in three sides of the outer case member 261, 262 in communication with the accommodation space 261S, 262S. The first and second outer case members 261 and 262 are electrically and hermetically joined together in such a manner as to accommodate the power supply circuits 210 and 240 surrounded by the inner circuit casing 250, the measurement circuit module 220 (signal current detection circuit 230) and the isolation transformer 270 in the accommodation spaces 261S and 262S and to hold the cable 160 and the connector 225 in the cable insertion grooves 261C and 262 and the connector installation grooves 261E and 262E, respectively.

The transfer pump 300 is equipped with an air supply pipe 310 and adapted to take in and compress ambient air, and then, eject clean compressed air AR (as a high-pressure gas) to the fine particle sensor 10 through the air supply pipe 310.

As shown in FIGS. 1 and 7, the cable 160 is in the form of a double-shield cable having a power supply wiring line 161 and an auxiliary wiring line 162 shielded by two inner and outer shield lines 165 and 167. In the present embodiment, the cable 160 also has an air supply pipe 163 integrally incorporated inside the inner shield line 165.

The wiring lines 161 and 162 are each formed from e.g. a copper wire.

The air supply pipe 163 is formed of e.g. polytetrafluoroethylene (PTFE) into a hollow shape, thereby defining therethrough a gas flow passage 163H in a longitudinal direction of the cable 160.

The wiring lines 161 and 162 and the air supply pipe 163 are circumferentially surrounded by an inner insulating member 164. In the present embodiment, the inner insulating member 164 includes insulating coating layers 164a and 164b formed of e.g. PTFE or tetrafluoroethylene-hexafluoropropylene copolymer (FEP) around the wiring lines 161 and 162, respectively, an insulating fibrous material 164c applied around the coating layers 164a and 164b and the air supply pipe 163 and filled in spaces between the coating layers 164a and 164b and between the coating layer 164a, 164b and the air supply pipe 163, and an insulating coating layer 164d formed by winding an insulating tape of e.g. PTFE around the coating layers 164a and 164b, the air supply pipe 163 and the insulating fibrous material 164c. As the insulating fibrous material 164c, there can be used those containing e.g. glass fiber or cotton spinning fiber in such a manner that the extension direction of the fiber is in agreement with the longitudinal direction of the cable 160. Thus, the wiring line 161, 162 is surrounded by three components of the insulating member 164, that is, the coating layer 164a, 164b, the insulating material 164c and the coating layer 164d, and then, surrounded by the inner shield line 165.

The inner shield line 165 is formed by placing e.g. a braided wire of copper around the insulating member 164 (the coating layer 164d). An insulating inner-shield-line coating layer 166 of e.g. PTEF or FEP is applied to the inner shield line 165 so as to cover and protect the inner shield line 165 by the coating layer 166.

The outer shield line 167 is formed by placing e.g. a braided wire of copper around the inner-shield-line coating layer 166. An insulating outer-shield-line coating layer 168 of e.g. PTFE or FEP is applied to the outer shield line 167 so as to cover and protect the outer shield line 167 by the coating layer 168.

In this way, the wiring line 161, 162 is double-shielded by the inner and outer shield lines 165 and 167 through the insulating member 164 and the insulating coating layer 166.

As shown in FIGS. 1 to 4, the cable 160 is electrically connected with the sensor drive control device 200 and the transfer pump 300.

More specifically, a rear end portion of the cable 160 around which a waterproof/dustproof grommet 284 is attached is held in the cable insertion grooves 261C and 262C of the outer case members 261 and 262 of the outer circuit casing 260 and inserted into the inner circuit casing 250 (inner circuit case 251).

Within the inner circuit casing 250, an exposed rear end portion of the power supply wiring line 161 and an exposed rear end portion of the auxiliary wiring line 162 are connected to the second output terminal 212 of the ion-source power supply circuit 210 and the second output terminal 242 of the auxiliary-electrode power supply circuit 240, respectively. An exposed rear end portion 165T of the inner shield line 165 is held between the inner case members 252 and 253 so that the first output terminal 211 of the ion-source power supply circuit 210, the first output terminal 241 of the auxiliary-electrode power supply circuit 240, the signal input terminal 231 of the signal current detection circuit 230, the inner circuit casing 250 (inner circuit case 251) and the inner shield line 165 are electrically continuous with one another. An exposed rear end portion 167T of the outer shield line 167 is held between the outer case members 261 and 262 so that the ground input terminal 232 of the signal current detection circuit 230, the outer circuit casing 260 and the outer shield line 167 are electrically continuous with one another.

Further, a pipe joint 283 around which a waterproof/dustproof grommet 285 is attached is held in the joint insertion grooves 261D and 262D of the outer case members 261 and 262 and is inserted in the inner circuit casing 250 (inner circuit case 251).

A front end portion of the air supply pipe 310 of the transfer pump 300 is connected to the pipe joint 283, whereas a rear end portion of the air supply pipe 163 of the cable 160 is exposed and left open within the inner circuit casing 250 (inner circuit case 251). The air supply pipe 310 of the transfer pump 300 is thus brought into gas communication with the air supply pipe 163 of the cable 160 by the pipe joint 283 so that the compressed air AR discharged from the air supply pipe 310 of the transfer pump 300 flows into the air supply pipe 163 of the cable 160 through the inside of the inner circuit casing 250 (inner circuit case 251).

As shown in FIGS. 2 to 4, a rectangular flame-shaped insulating member 281 is fitted around one end of the inner circuit casing 250 (inner circuit case 251); and an insulating spacer member 282 is fitted around the other end of the inner circuit casing 250 (inner circuit case 251) with the cable 160 passing through an insertion hole 282H of the insulating spacer 282. Both of the insulating members 281 and 282 are formed of insulating resin and arranged in the accommodation spaces 261S and 262S of the outer circuit casing 260. By these insulating members 281 and 282, the inner circuit casing 250 is supported in a floated state within the outer circuit casing 260 and is thereby spaced apart and insulated from the outer circuit casing 260 whereby the opposing surfaces 271AS and 271BS of the primary and secondary cores 271A and 271B are located adjacent to each other but kept away and insulated from each other.

As shown in FIGS. 1, 5, 6 and 8, the fine particle sensor 10 is inserted in a mounting hole EPO of the mounting portion EPT of the exhaust pipe EP, with a front end portion of the fine particle sensor 10 situated inside the exhaust pipe EP and a rear end portion of the fine particle sensor 10 connected to a front end portion 160S of the cable 160. (In FIGS. 5, 6 and 8, the top and bottom sides correspond to the front and rear sides, respectively.) The fine particle sensor 10 has four electrical function units: an ion/gas ejection unit 11, a particle charging unit 12, an inner sensor casing 13 and an outer sensor casing 14. These electrical function units 11, 12, 13 and 14 extend over mechanical structural components of the fine particle sensor 10.

The mechanical structure (structural components) of the fine particle sensor 10 will be first explained below.

In the fine particle sensor 10, a needle-shaped electrode member 20 is formed from e.g. a tungsten wire and connected at a rear end thereof to an exposed front end portion of the power supply wiring line 161 of the cable 160. As shown in FIGS. 5 and 6, the needle-shaped electrode member 20 has a substantially straight rod-shaped extending portion 21 and a needle-like pointed front end portion 22 located front of the extending portion 21. The extending portion 21 of the needle-shaped electrode member 20 is covered with a cylindrical insulating ceramic pipe 75.

Further, an auxiliary electrode member 50 is formed from e.g. a stainless wire and connected at a rear end thereof to an exposed front end portion of the auxiliary wiring line 162 of the cable 160. As also shown in FIGS. 5 and 6, the auxiliary electrode member 50 has a substantially straight rod-shaped extending portion 51, a U-bent portion 52 located front of the extending portion 51 and an electrode portion 53 extending from the U-bent portion 52 in parallel with the extending portion 51 and formed with a needle-like pointed end 53S. As will be discussed later, the electrode portion 53 of the auxiliary electrode member 50 serves as an auxiliary electrode to assist in ion trapping function. (The electrode portion 53 is hence sometimes referred to as "auxiliary electrode 53".) The extending portion 51 of the auxiliary electrode member 50 is covered with a cylindrical insulating ceramic pipe 77.

A holder member 60 of e.g. stainless steel is disposed circumferentially around the electrode members 20 and 50. As shown in FIGS. 5, 6 and 8, the holder member 60 has a solid cylindrical column-shaped holding portion 61, a hollow cylindrical wall portion 63 extending toward the front from a front circumferential edge of the holding portion 61 and an annular flange portion 66 protruding radially outwardly from an outer circumferential surface of the holding portion 61. Insertion holes 61H and 61I are axially formed in the holding portion 61 so that the ceramic pipes 75 and 77 are hermetically inserted in the insertion holes 61H and 61I, respectively, to hold the electrode members 20 and 50 in the holding portion 61 in such a manner that the front end portion 22 of the needle-shaped electrode member 20 extends inside the cylindrical wall portion 63. An air supply hole 61J is also formed through the holding portion 61 in parallel with the insertion holes 61H and 61I.

A metallic cylindrical inner tube 80 is fitted around a rear end portion of the holder member 60 and around a front end portion 164dS of the insulating coating layer 164d of the insulating member 164 of the cable 160. Further, a rear end of the inner tube 80 is electrically connected by crimping onto an exposed front end portion of the inner shield line 165 of the cable 160. By engagement of the holder member 60 with the inner tube 80, the holder member 60 is fixed in position and made electrically continuous with the inner shield line 165 of the cable 160 through the inner tube 80.

As shown in FIGS. 6 and 8, a front end potion 163s of the air supply pipe 163 of the cable 160 is exposed and left open within the inner tube 80 so that the compressed air AR supplied from the transfer pump 300 through the air supply pipe 163 of the cable 160 flows into the air supply hole 61J of the holder member 60 through the inside of the inner tube 80.

A bottomed-cylindrical nozzle member 30 of e.g. stainless steel is fitted in a front end of the cylindrical wall portion 63 of the holder member 60. As shown in FIGS. 5, 6 and 8, the nozzle member 30 has a nozzle portion 31 located at the bottom thereof and a hollow cylindrical wall portion 33 extending toward the front from a front circumferential edge of the nozzle portion 31. The nozzle portion 31 has an inner surface 31T tapered toward the front in such a manner as to define a fine through hole as a nozzle 31N in the center of the bottom portion 31. Further, a gas inlet hole 331 is formed through the cylindrical wall portion 33. By engagement of the nozzle member 30 with the holder member 60, the nozzle member 30 is fixed in position and made electrically continuous with the inner shield line 165 of the cable 160 through the holder member 60 and the inner tube 80.

As shown in FIGS. 5 and 6, there is a discharge space DS defined by the nozzle portion 31 of the nozzle member 30 and the cylindrical wall portion 63 of the holder member 60 upon engagement of the nozzle portion 31 in the cylindrical wall portion 63. In this discharge space DS, the front end portion 22 of the needle-shaped electrode member 20 protrudes from the holding portion 61 of the holder member 60 and faces but is spaced apart from the tapered surface 31T (nozzle 31N) of the nozzle portion 31 of the nozzle member 30. This discharge space DS is in gas communication with the air supply hole 61J of the holder member 60.

A mixing/discharging member 40 of e.g. stainless steel is fitted in a front end of the cylindrical wall portion 33 of the nozzle member 30. As shown in FIGS. 5, 6 and 8, the mixing/discharging member 40 has a rear end portion 41 and a hollow cylindrical wall portion 43 extending toward the front from a front circumferential edge of the rear end portion 41. A front end of the cylindrical wall portion 43 is closed by a cap member 48. A gas outlet hole 43O is formed through the cylindrical wall portion 43. An inner surface of the rear end portion 41 protrudes partially radially inwardly to form a trapping electrode 42 in such a manner that an inner space of the rear end portion 41 is narrowed in a slit-like form by the trapping electrode 42, whereas a cylindrical inner space is defined by an inner surface of the cylindrical wall portion 43. Further, a cut 42K is formed in the trapping electrode 42 at a position corresponding to the gas inlet hole 331 of the nozzle member 33. By engagement of the mixing/discharging member 40 with the nozzle member 30, the mixing/discharging member 40 is fixed in position and made electrically continuous with the inner shield line 165 of the cable 160 through the nozzle member 30, the holder member 60 and the inner tube 80.

As shown in FIGS. 5 and 6, there is a mixing space MX defined by the nozzle portion 31 and the cylindrical wall portion 33 of the nozzle member 30 and the rear end portion 41 of the mixing/discharging member 40 upon engagement of the rear end portion 41 in the cylindrical wall portion 33. The mixing space MX is herein divided into first and second mixing regions MX1 and MX2. The first mixing region MX1 refers to a substantially cylindrical space formed by a front end surface 31S of the nozzle portion 31, an inner circumferential surface of the cylindrical wall portion 33 and a rear end surface of the rear end portion 41 (trapping electrode 42). The second mixing region MX2 refers to a slit-like inner space formed by the trapping electrode 42 inside the rear end portion 41.

A gas discharge passage EX is defined by a front end surface of the rear end portion 41, an inner circumferential surface of the cylindrical wall portion 43 and a rear end surface of the cap member 48 so as to provide gas communication from the mixing space MX (second mixing region MX2) to the gas outlet hole 43. A gas introduction passage HK is defined by the cut 42K so as to provide gas communication from the gas inlet hole 331 to the mixing space MX (first mixing region MX1).

The extending portion 51 of the auxiliary electrode member 50 covered with the insulating ceramic pipe 77 extends through the holder member 60 and the nozzle member 30 in such a manner that: the U-bent portion 52 of the auxiliary electrode member 50 is located inside the gas discharge passage EX; and the electrode portion 53 of the auxiliary electrode member 50 extends inside the second mixing region MX2 and is surrounded by the rear end portion 41 (trapping electrode 42) of the mixing/discharging member 40.

A substantially cylindrical first insulating ceramic spacer 121 of e.g. alumina is arranged on a front side of the flange portion 66 of the holder member 60. Further, a substantially cylindrical second insulating ceramic spacer 122 of e.g. alumina is arranged on a rear side of the flange portion 66 of the holder member 60.

A metal shell 90 of e.g. stainless steel is disposed circumferentially around the first and second insulating ceramic spacers 121 and 122. As shown in FIGS. 5 and 8, the metal shell 90 includes a cylindrical portion 91 and a substantially ellipse plate-shaped flange portion 95 protruding radially outwardly from a front end of the cylindrical portion 91. A spacer retaining hole 91H is formed in the cylindrical portion 91 so that the first and second insulating ceramic spacers 121 and 122 are retained in the spacer retaining hole 91H. A female thread 92 is formed in an inner circumferential surface of the cylindrical portion 91. As shown in FIGS. 6 to 8, two bolt holes 95H are formed through the flange portion 95 in a thickness direction of the flange portion 95.

A metallic plug member 100 is screwed in a rear end of the cylindrical portion 91 of the metal shell 90. More specifically, a male thread 102 is formed on an outer circumferential surface of the plug member 100 and tightened into the female thread 92 of the cylindrical portion 91 of the metal shell 90. The plug member 100 is cylindrical in shape so that the inner tube 80 is inserted in the plug member 100 but is kept in non-contact with the plug member 100. As shown in FIGS. 5, 6 and 8, the plug member 100 has a pressing portion 101 formed with a flat front end surface 101S at a position front of the male thread 102 and protruding axially toward the front and a hexagonal portion 103 formed with a hexagonal outer circumference at a position rear of the male thread 102 and protruding radially outwardly in a flange form.

By engagement of the male thread 102 and the female thread 92, the plug member 100 shifts toward the front. Then, the pressing portion 101 of the plug member 100 comes into contact with and presses the second insulating ceramic spacer 122 toward the front. As the second insulating ceramic spacer 122 presses the flange portion 66 of the holder member 60 toward the front, the flange portion 66 of the holder member 60 presses the first insulating ceramic spacer 121 toward the front so that the first insulating ceramic spacer 121 fits in the cylindrical portion 91 of the metal shell 90 through a plate packing 124. With this, the holder member 60, the first insulating ceramic spacer 121, the second insulating ceramic spacer 122, the plate packing 124 and the plug member 100 are held in the metal shell 90 and assembled together as one unit. As the first and second insulating ceramic spacers 121 and 122 are disposed between the holder member 60 and the metal shell 90, the holder member 60 and the metal shell 90 are spaced apart and kept insulated from each other by these insulating ceramic spacers 121 and 122.

For mounting of the fine particle sensor 10, the metal shell 90 is fixed to the sensor mounting portion EPT of the exhaust pipe EP by inserting the front end portion (i.e. the nozzle member 30, the mixing/discharging member 40 etc.) of the fine particle sensor 10 in the exhaust pipe EP from through the mounting hole EPO, passing stud bolts EPB through the bolt holes 95H of the flange portion 95, and then, tightening nuts EPN onto the stud bolts EPB as shown in FIG. 6. An annular gasket retaining hole 96 is formed in a front surface 90S of the metal shell 90 at a position radially outside of the retaining hole 9111 so that a copper gasket 130 is retained in the gasket retaining hole 96 and held between the metal shell 90 and the sensor mounting portion EPT of the exhaust pipe EP. The gasket 130, the metal shell 90 and the plug member 100 are thus set to the same ground potential PVE as the exhaust pipe EP.

A cylindrical outer tube 110 of e.g. stainless steel is fitted on a rear end portion 104 of the plug member 100 so as to surround the inner tube 80 and the front end portion 160S of the cable 160 from the radially outer side. Herein, the entire circumference of a front end portion 110S of the outer tube 110 is laser welding to the rear end portion 104 of the plug member 100. The outer tube 110 has a rear end portion 110*k* decreasing in outer diameter toward the rear. The rear end portion 110*k* of the outer tube 110 is crimped onto the cable 160 to form a crimped region 110*kk* in such a manner that the crimped region 110*kk* passes through the outer-shield-line coating layer 168 of the cable 160 and comes into electrical conduction with the outer shield line 167 of the cable 160. The outer tube 110 and the outer shield line 167 are thus set to the same ground potential PVE as the exhaust pipe EP through the metallic structural components, i.e., the metal shell 90, the plug member 100 and the gasket 130.

A cylindrical grommet 125 of insulating rubber is disposed between the front end portion 160S of the cable 160 and the outer tube 110 in order to prevent the front end portion 160S of the cable 160 from swinging within the outer tube 110.

Next, the operations of the fine particle detection system 1 and the electrical function units of the fine particle sensor 10 will be explained below with reference to FIG. 9. (As FIG. 9 is schematically illustrated for ease of understanding of the electrical function units and operation of the fine particle sensor 10, some parts in FIG. 9 may be seen different in configuration from those in the other drawings.)

As the needle-shaped electrode member 20 is connected to and electrically continuous with the second output terminal 212 of the ion-source power supply circuit 210 through the power supply wiring line 161 of the cable 160, the needle-shaped electrode member 20, the second output terminal 212 of the ion source power supply circuit 210 and the power supply wiring line 160 of the cable 160 are set to the second floating potential PV2.

The auxiliary electrode member 50 (auxiliary electrode 53), the second output terminal 242 of the auxiliary-electrode power supply circuit 240 and the auxiliary wiring line 162 of the cable 160 are set to the third floating potential PV3 as the auxiliary electrode member 50 is connected to and electrically continuous with the second output terminal 242 of the auxiliary-electrode power supply circuit 240 through the auxiliary wiring line 162 of the cable 160.

The inner tube 80, the holder member 60, the nozzle member 30, the mixing/discharging member 40 (trapping electrode 42), the first output terminal 211 of the ion-source power supply circuit 210, the first output terminal 241 of the auxiliary-electrode power supply circuit 240, the signal output terminal 231 of the signal current detection circuit 230, the inner circuit casing 250 and the inner shield line 165 of the cable 160 are set to the first floating potential PV1 as the inner tube 80, the holder member 60, the nozzle member 30 and the mixing/discharging member 40 are connected to and electrically continuous with the first output terminal 211 of the ion-source power supply circuit 210, the first output terminal 241 of the auxiliary-electrode power supply circuit 240, the signal output terminal 231 of the signal current detection circuit 230 and the inner circuit casing 250 through the inner shield line 165 of the cable 160.

As mentioned above, the effective potential values of the first, second and third floating potentials PV1, PV2 and PV3 are preferably set to satisfy the relationship of PV1<PV3<PV2.

Further, the outer tube 110, the plug member 100, the metal shell 90 and the gasket 130 are connected to and electrically continuous with the ground input terminal 232 of the signal current detection circuit 230 through the outer shield line 167 of the cable 160 so that the outer tube 110, the plug member 100, the metal shell 90, the gasket 130, the ground input terminal 232 of the signal current detection circuit 230 and the outer shield line 167 of the cable 160 are set to the same ground potential PVE as the exhaust pipe EP.

As the needle-shaped electrode member 20 is set higher in potential than the nozzle member 30 as mentioned above, the front end portion 22 of the needle-shaped electrode member 20 and the nozzle portion 31 (taper surface 31T) of the nozzle member 30 function as a positive electrode (also referred to as "second electrode") and a negative electrode (also referred to as "first electrode"), respectively. In this configuration, there arises aerial discharge in the discharge space DS with the application of a high voltage (potential difference) of e.g. 1 to 2 kV between the nozzle portion 31 of the nozzle member 30 and the front end portion 22 of the needle-shaped electrode member 20 by the ion-source power supply circuit 210 through the cable 160. In the occurrence of the aerial discharge, positive ions CP such as $N^{3+}$ and $O^{2+}$ are generated in the discharge area DS by dissociation of $N_2$, $O_2$ etc. in the air.

As the aerial discharge, corona discharge can suitably be adopted. In the present embodiment, positive needle corona discharge PC is generated around the needle-like pointed front end portion 22 of the electrode member 20 as the needle-like pointed front end portion 22 of the needle-shaped electrode member 20 is opposed to and spaced apart from the taper surface 31T of the nozzle portion 31 of the nozzle member 30. It is possible to continuously and efficiently generate the positive ions PC from the gas (air) by such positive needle corona discharge PC.

Further, the compressed air AR is supplied from the transfer pump 300 to the discharge area DS through the air supply pipe 163 of the cable 160.

The generated positive ions CP and the compressed air AR are ejected at a high speed into the mixing space MX through the nozzle 31N.

It is thus understood that, in the present embodiment, the holding portion 61 and cylindrical wall portion 63 of the holder member 60 and the nozzle portion 31 of the nozzle member 30 and the needle-shaped electrode member 20 constitute the ion/gas ejection unit 11 which functions as an ion source unit to generate and eject the positive ions CP into the mixing space MX and also functions as a gas ejection unit to eject the air AR into the mixing space MX.

Upon ejection of the air AR into the mixing space MX, the pressure inside the mixing space MX (first mixing region MX1) is lowered. The exhaust gas EG is then introduced by suction from the exhaust pipe EP into the mixing space MX (first and second mixing regions MX1 and MX2) through the gas inlet hole 331 and the gas introduction passage HK. The introduced exhaust gas EGI and the air AR ejected with the positive ions CP are mixed together in the mixing space MX, fed from the mixing space MX (first and second mixing regions MX1 and MX2) to the discharge passage EX, and then, discharged out from the discharge passage EX to the exhaust pipe EP through the gas outlet hole 43O.

When fine particles (e.g. soot) S are present in the exhaust gas EG, some of the positive ions CP are adsorbed onto the fine particles S so that the fine particles S are charged by the positive ions CP.

The resulting positively charged particles SC are discharged to the exhaust pipe EP through the mixing space MX, the discharge passage EX and the gas outlet hole 43 according to the flow of the exhaust gas EGI and the air AR.

By contrast, many remainder of the positive ions CP are left as stray ions CPF without being adsorbed onto the fine particles S.

As the auxiliary electrode member 50 is set higher in potential than the mixing/discharging member 40 as mentioned above, the electrode portion (auxiliary electrode) 53 of the auxiliary electrode member 50 and the rear end portion 41 and cylindrical wall portion 43 of the mixing/discharging member 40 (trapping electrode 42) function as a positive electrode and a negative electrode, respectively. By the supply of power from the auxiliary-electrode power supply circuit 240 through the cable 160, there is exerted a repulsive force on the stray ions CPF from the electrode portion (auxiliary electrode) 53 of the auxiliary electrode member 50 so that the stray ions CPF are diverted outwardly by the electrode portion (auxiliary electrode) 53 of the auxiliary electrode member 50 and trapped by the rear end portion 41 and cylindrical wall portion 43 of the mixing/discharging member 40 (trapping electrode 42).

It is thus understood that: the cylindrical wall portion 33 of the nozzle member 30, the mixing/discharging member 40 and the cap member 48 constitute the particle charging unit 12.

In the present embodiment, the holding portion 61 of the holder member 60 and the inner tube 80 are electrically continuous with the nozzle portion 31 of the nozzle member 30 but are electrically insulated from the needle-shaped electrode member 20 and the exhaust pipe EP. Further, the holding portion 61 of the holder member 60 and the inner tube 80 are located at a position nearer to the cable 160 than the particle charging unit 12 and the ion/gas ejection unit 11 so as to circumferentially surround the needle-shaped electrode member 20 (extending portion 21). It is thus understood that the holding portion 61 of the holder member 60 and the inner tube 80 constitute the inner sensor casing 13.

On the other hand, the cylindrical portion 91 of the metal shell 90, the plug member 100 and the outer tube 110 are electrically continuous with the exhaust pipe EP (i.e. connected to the ground potential PVE) but are electrically insulated from the particle charging unit 12 and the inner sensor casing 13. Further, the cylindrical portion 91 of the metal shell 90, the plug member 100 and the outer tube 110 are located so as to circumferentially surround and electromagnetically shield parts of the particle charging unit 12, the ion/gas ejection unit 11 and the inner sensor casing 13 located outside the exhaust pipe EP (such as the extending portion 21 of the needle-shaped electrode member 20, the extending portion of the auxiliary electrode member 50, the holding portion 61 of the holder member 60 and the inner tube 80). It is thus understood that the cylindrical portion 91 of the metal shell 90, the plug member 100 and the outer tube 110 constitute the outer sensor casing 14 in the present embodiment.

Furthermore, the double-shield cable 160 corresponds to a lead in which: the power supply wiring line 161 is electrically continuous with the needle-shaped electrode member 20 (second electrode) and with the inner sensor casing 13 (inner tube 80); the inner shield line 165 is kept insulated from but circumferentially surrounds the power supply wiring line 161; and the outer shield line 167 is electrically continuous with the outer sensor casing 14 (the outer tube 110) and is kept insulated from but circumferentially surrounds and electromagnetically shields the inner shield line 165 (and the wiring lines 161 and 162 inside the inner shield line 165).

In the above-structured fine particle detection system 1, a discharge current Id flows from the second output terminal 212 of the ion-source power supply circuit 210 to the needle-shaped electrode member 20 (second electrode) through the power supply wiring line 161, as shown in FIG. 1, for generation of the aerial discharge in the ion/gas ejection unit 11. The major part of the discharge current Id flows, as an incoming current Ij, to the nozzle portion 31 of the nozzle member 30 (first electrode), and then, to the first output terminal 211 of the ion-source power supply circuit 210 through the inner shield line 165. Further, there arises a trapping current Ih due to the flow of charge of the stray ions CPF trapped by the trapping electrode 42 in the particle charging unit 12. The trapping current Ih flows from the particle charging unit 12 to the first output terminal 211 of the ion-source power supply circuit 210 through the inner shield line 165. Accordingly, the sum of the incoming current Ij and the trapping current Ih (referred to as "incoming/trapping current Ijh") flows through the inner shield line 165.

There also arises an electric current due to the flow of charge of the positive ions CPH of the charged fine particles SC when the charged fine particles SC are discharged to the exhaust pipe EP through the gas outlet hole 43O. (The exhaust pipe EP into which the charged fine particles SC are discharged is set to the ground potential PVE.)

The incoming/trapping current Ijh is slightly smaller than the discharge current Id by such a current due to the flow of the positive ions CPH of the charged fine particles SC discharged to the exhaust pipe EP. This leads to an unbalance between the discharge current Id flowing out from the second output terminal 212 of the ion-source power supply circuit 201 and the incoming/trapping current Ijh flowing in the first output terminal 211 of the ion-source power supply circuit 210.

In order to balance between the discharge current Id and the incoming/trapping current Ijh, a current Is flows between the ground potential PVE and the first output terminal 211 of the ion-source power supply circuit 210. This current Is is detected as the signal current by the signal current detection circuit 230 as the signal current detection circuit 230 has its signal and ground input terminals 231 and 232 connected to the first output terminal 211 of the ion-source power supply circuit 210 and the ground potential PVE, respectively.

The intensity of the signal current Is (=Id−Ijh) is responsive to the amount of the positive ions CPH of the discharged charged fine particles SC, that is, the amount of the fine particles S in the introduced exhaust gas EGI and, by extension, the amount of the fine particles S in the exhaust gas EG flowing through the exhaust pipe EP. The amount of the fine particles in the exhaust gas EG can be thus determined by detection of the signal current Is.

However, the signal current Is is of the order of pA when the discharge current Id is of the order of μA. There is a large possibility that the intensity of the signal current Is varies under the influence of a leakage current and electromagnetic noises.

The influence of the leakage current on the signal current Is will be now discussed below.

As mentioned above, it is necessary to apply a high voltage of e.g. 1 to 2 kV between the front end portion 22 of the needle-shaped electrode member 20 (second electrode) and the nozzle portion 31 of the nozzle member 30 (first electrode) for generation of the aerial discharge in the ion/gas ejection unit 11. In other words, the second floating potential PV2 of the needle-shaped electrode member 20 is set to a positive potential value higher than the first floating potential PV1 of the nozzle member 30. However, a part of the discharge current Id leaks out as a leakage current from such a higher-potential electrode member 20 (second electrode) or the system structural component or wiring line electrically continuous therewith (such as the power supply wiring line 161 or the second output terminal 212 of the ion-source power supply circuit module 220).

If the leakage current flows into any system structural component or wiring line set to the first floating potential PV1 (such as the inner sensor casing 13, the inner shield line 165 or the inner circuit casing 250), the leakage current finally returns to the first output terminal 211 of the power supply circuit 210 and does not cause a change in the intensity of the incoming/trapping current Ijh. There is no influence on the difference between the discharge current Id and the incoming/trapping current Ijh, i.e., on the intensity of the signal current Is. In this case, the occurrence of the leakage current become a significant problem and merely results in a decrease of the amount of electric current actually used for the discharge.

If the leakage current flows into any system structural component or wiring line set to the ground potential PVE (such as the outer sensor casing 14, the outer shield line 167 or the outer circuit casing 260), by contrast, the leakage current does not return to the first output terminal 211 of the power supply circuit 210. The incoming/trapping current Ijh becomes apparently so small as to cause an increase of the difference between the discharge current Id and the incoming/trapping current Ijh, i.e., an increase of the intensity of the signal current Is. As the intensity of the signal current Is is at a very low level of the order of pA as mentioned above, the leakage of even a very small current to the ground potential PVE results in a large error in the signal current Is.

The influence of the electromagnetic noises on the signal current Is will be next discussed below.

The intensity of the discharge current Id or the intensity of the incoming/trapping current Ijh becomes apparently changed when electromagnetic noises are superimposed on the passage of the discharge current Id (such as the power supply wiring line 161) or on the passage of the incoming/trapping current Ijh (such as the inner shield line 165). This causes a variation in the difference between the discharge current Id and the incoming/trapping current Ijh, i.e., in the intensity of the signal current Is. As the intensity of the signal current Is is at a very low level of the order of pA, the occurrence of even a small change in the discharge current Id or incoming/trapping current Ijh results in a large error in the signal current Is.

In the present embodiment, the inner sensor casing 13 is electrically continuous with the nozzle portion 31 of the nozzle member 30 (first electrode) and is located nearer to the cable 160 than the particle charging unit 12 and the ion/gas ejection unit 11 so as to circumferentially surround the needle-shaped electrode member 20 (second electrode); the inner shield line 165 is electrically continuous with the nozzle portion 31 of the nozzle member 30 (first electrode) and the inner sensor casing 13 and is located so as to circumferentially surround the power supply wiring line 161; and the inner circuit casing 250 (inner circuit case 251 and primary core 271A) is electrically continuous with the first output terminal 211 of the ion-source power supply circuit 210 and is located so as to surround the ion-source power supply circuit 210.

Even if a part of the discharge current Id leaks out as a leakage current from the system structural component or wiring line set to the second floating potential PV2 (such as the needle-shaped electrode member 20 (second electrode), the power supply wiring line 165 or the second output terminal 212 of the ion-source power supply circuit 210), the present fine particle detection system 1 allows the leakage current to flow into the inner sensor casing 13, the inner shield line 165 or the inner circuit casing 250, and then, flow as the incoming/trapping current Ijh to the first output terminal 211 of the ion-source power supply circuit 210. The leakage current does not flow in any system structural component or wiring line outside of the inner sensor casing 13, the inner shield line 165 and the inner circuit casing 250 (such as the outer sensor casing 14, e.g., the metal shell 90 etc., the outer wiring line 167 or the outer circuit casing 260). It is therefore possible in the present embodiment to prevent a change in the incoming/trapping current Ijh, i.e., a variation in the signal current Is caused by the leakage current.

In addition, the outer sensor casing 14 is electrically continuous with the exhaust pipe EP (the ground potential PVE) and is located so as to circumferentially surround the parts of the particle charging unit 12, the ion/gas ejection unit 11 and the inner sensor casing 13 located outside the exhaust pipe EP (such as the extending portion 21 of the needle-shaped electrode member 20, the extending portion 53 of the auxiliary electrode member 50, the holding portion 61 of the holder member 60 and the inner tube 80). It means that: the needle-shaped electrode member 20 (second electrode) is electromagnetically double-shielded by the inner and outer sensor casings 13 and 14; and the part of the inner sensor casing 13 located outside the exhaust pipe EP is electromagnetically single-shielded by the outer sensor casing 14. The outer shield line 167 is electrically continuous with the exhaust pipe EP and the outer sensor casing 14 (the ground potential PVE) and is located so as to circumferentially surround the power supply wiring line 161 covered with the inner shield line 165. It means that: the power supply wiring line 161 is electromagnetically double-shielded by the inner and outer shield lines 165 and 167; and the inner shield line 165 is electromagnetically single-shielded by the outer shield line 167. Further, the outer circuit casing 160 is electrically continuous with the exhaust pipe EP (the ground potential PVE) and located so as to surround the ion-source power supply circuit 210 accommodated in the inner circuit casing 250 and the signal current detection circuit 230. It means that: the ion-source power supply circuit 210 is electromagnetically double-shielded by the inner and outer circuit casings 250 and 260; and the signal current detection circuit 230 is electromagnetically single-shielded by the outer circuit casing 260.

By these electromagnetic shield effects of the outer sensor casing 14, the outer shield line 167 and the outer circuit casing 260, it becomes unlikely that both of the discharge current Id flowing between the second output terminal 212 of the ion-source power supply circuit 210 and the needle-shaped electrode member 20 (second electrode) and the incoming/trapping current Ijh flowing between the first output terminal 211 of the ion-source power supply circuit 210 and the nozzle portion 31 of the nozzle member 30 (first electrode) or the trapping electrode 42 will be influenced by the external electromagnetic noises. It is therefore possible in the present embodiment to prevent a variation in the signal current Is caused by superimposing of the electromagnetic noises.

Accordingly, the present fine particle detection system 1 is able to detect the intensity of the signal current Is accurately without the influence of the leakage current and electromagnetic noises and determine the amount of the fine particles S in the exhaust gas EG properly.

If the stray ions CPF are discharged to the exhaust pipe EP from the gas outlet hole 43O without being trapped by the trapping electrode 42, the trapping current Ih (incoming/trapping current Ijh) becomes decreased to cause an increase of the signal current Is. In this case, the signal current Is contains a component irrelevant to the amount of the fine particles S. The accuracy of detecting the amount of the fine particles S deteriorates due to such an irrelevant component in the signal current Is.

In the present embodiment, the auxiliary electrode member 50 (auxiliary electrode 53) is connected to the third floating potential PV3 and arranged in the slit-like mixing region MX2 of the mixing space MX. As the third floating potential PV3 is set to a positive direct-current potential value higher than the first floating potential PV1 as mentioned above, the stray ions CPF can be, diverted to the trapping electrode 42 under the repulsive force from the auxiliary electrode member 50 (auxiliary electrode 53) so that it is possible to trap the stray ions CPF by the trapping electrode 42 more efficiently and assuredly. Namely, the auxiliary electrode 53 is arranged in the particle charging unit 12 so as to assist in the ion trapping function of the trapping electrode 24.

As mentioned above, the auxiliary electrode member 50 (auxiliary electrode 53) is electrically continuous with the second output terminal 242 of the auxiliary-electrode power supply circuit 240 through the auxiliary wiring line 162 while being electrically insulated from the needle-shaped electrode member 200 and the nozzle portion 31 of the nozzle member 30. Further, the portion of the auxiliary electrode member 50 located nearer to the cable 160 than the ion/gas ejection unit 11 and the particle charging unit 12, the auxiliary wiring line 162 and the auxiliary-electrode power supply circuit 240 are surrounded by the inner sensor casing 13, the inner shield line 165 and the inner circuit casing 250, respectively. As the inner sensor casing 13, the inner shield line 165 and the inner circuit casing 250 are surrounded and electromagnetically shielded by the outer sensor casing, 14, the outer shield line 176 and the outer circuit casing 260, the portion of the auxiliary electrode member 50 located nearer to the cable 160 than the particle charging unit 10, the auxiliary wiring line 162 and the auxiliary-electrode power supply circuit 240 are surrounded and electromagnetically shielded by the outer sensor casing, 14, the outer shield line 176 and the outer circuit casing 260. It is thus possible to prevent superimposing of the external electromagnetic noises onto the auxiliary electrode member 50 (auxiliary electrode 53), the auxiliary wiring line 162 and the auxiliary-electrode power supply circuit 240 so that the trapping of the stray ions CPF by the trapping electrode 42 would not be affected due to a change of the third floating potential PV3 under the influence of the electromagnetic noises.

There may also occur a leakage current from the system structural component or wiring line set to the third floating potential PV3 (such as the auxiliary electrode member 50, the auxiliary wiring line 162 or the second output terminal 242 of the auxiliary-electrode power supply circuit 240). If this leakage current flows in the system structural component or wiring line set to the ground potential PVE (such as the outer sensor casing 14, the outer shield line 167 or the outer circuit casing 260), the leakage current returns to the first output terminal 241 of the auxiliary-electrode power supply circuit 240 through the signal current detection circuit 230 and thereby affects the accuracy of detection of the signal current Is.

In the present embodiment, the system structural component or wiring line set to the second floating potential PV2 (such as the auxiliary electrode member 50, the auxiliary wiring line 162 and the auxiliary-electrode power supply circuit 240) is surrounded by any of the inner sensor casing 13, the inner shield line 165 and the inner circuit casing 250 each set to the first floating potential PV1. The leakage current does not reach any system structural component or wiring line outside of the inner sensor casing 13, the inner shield line 165 and the inner circuit casing 250 (such as the outer sensor casing 14, the outer shield line 167 and the outer circuit casing 260). The occurrence of such a leakage current merely leads to an increase of the amount of electric current flowing out from the second output terminal 242 of the auxiliary-electrode power supply circuit 240. It is thus possible in the present embodiment to prevent the signal current Is from being influenced by the leakage current even when the leakage current occurs from the system structural component or wiring line set to the third floating potential PV3 (such as the auxiliary electrode member 50, the auxiliary wiring line 162 or the auxiliary-electrode power supply circuit 240).

As the first output terminal 241 of the auxiliary-electrode power supply circuit 240 is electrically continuous with the inner shield line 165, the first output terminal 241 of the auxiliary-electrode power supply circuit 240 can be set to the same (common) potential PV1 as the first output terminal 211 of the ion-source power supply circuit 210 and the sensor structural component electrically connected thereto (such as the nozzle member 30). It is thus possible to easily set the relationship of the first, second and third floating potentials PV1, PV2 and PV3.

In the present embodiment, the ion-source power supply circuit 210 is supplied with power from the measurement circuit module 220 through the isolation transformer 270 so that the ion-source power supply circuit 210 and the first and second output terminals 211 and 212 of the ion-source power supply circuit 210 can be easily made floating with respect to the external potential (e.g. the ground potential PVE of the exhaust pipe EP). It is thus possible to easily set the first output terminal 211 of the ion-source power supply circuit 210 and the system structural component or wiring line electrically continuous therewith (such as the nozzle member 30 (first electrode)) to the first floating potential PV1 and set the second output terminal 212 of the ion-source power supply circuit 210 and the system structural component or wiring line electrically connected therewith (such as the needle-shaped electrode member 20 (second electrode)) to the second floating potential PV2. As the isolation transformer 270 is surrounded and electromagnetically shielded by the outer circuit casing 260, it is possible to prevent the external electromagnetic noises from entering into the ion-source power supply source 210 through the isolation transformer 270.

The auxiliary-electrode power supply circuit 240 is also supplied with power from the measurement circuit module 220 through the isolation transformer 270 so that the auxiliary-electrode power supply circuit 240 and the first and second output terminals 241 and 242 of the auxiliary-electrode power supply circuit 240 can be easily made floating with respect to the external potential (e.g. the ground potential PVE of the exhaust pipe EP). It is thus possible to easily set the first output terminal 241 of the auxiliary-electrode power supply circuit 240 to the first floating potential PV1 and set the second output terminal 242 of the auxiliary-electrode power supply circuit 240 and the system structural component or wiring line electrically connected therewith (such as the auxiliary electrode member 50) to the third floating potential PV3. It is further possible to prevent the external electromagnetic noises from entering into the auxiliary-electrode power supply source 240 through the isolation transformer 270 as the isolation transformer 270 is surrounded and electromagnetically shielded by the outer circuit casing 260.

Further, the separable primary and secondary cores 271A and 271B are provided in the isolation transformer 270. It is thus possible to limit the influence of the external noises on the ion-source power supply circuit 210 and the like by setting the primary and secondary cores 271A and 271B to the respective potential values. It is also possible to achieve easy insulation between the primary core 271A and the primary coil 272.

In general, the flow of the exhaust gas EG in the exhaust pipe EP is pulsing because of the properties of the internal combustion engine. For example, the flow of the exhaust is intermittent in the case of four-cycle engine. Further, the rate of flow of the exhaust gas EG in the exhaust pipe EP changes with the operating conditions of the internal combustion engine (such as engine revolution speed). It is likely that the amount of the introduced exhaust gas EGI will change if the exhaust gas EG is introduced into the particle charging unit 12 according to the flow of the exhaust gas EG in the exhaust pipe EP. This leads to a variation in the signal current Is.

In the present embodiment, however, the fine particle sensor 11 is so structured that: the ion/gas ejection unit 11 performs the function of the gas ejection unit to eject the compressed air AR (gas) into the mixing space MX; and the particle charging unit 12 introduces the exhaust gas EG by suction into the mixing space MX through the gas inlet hole 331 upon the ejection of the compressed air AR from the ion/gas ejection unit 11, mixes the introduced exhaust gas EGI with the ions CP, and then, discharge the exhaust gas EGI together with the compressed air AR to the exhaust pipe EP through the gas outlet hole 43O. As the particle charging unit 12 allows introduction of the exhaust gas EG by suction into the mixing space MX upon the ejection of the compressed air AR from the ion source unit (gas ejection unit) 11, it becomes unlikely that the amount of the introduced exhaust gas EGI will change according to the rate of flow of the exhaust gas EG in the exhaust pipe EP. It is thus possible to prevent a variation in the signal current Is due to such a change in the amount of the introduced exhaust gas EGI and possible to determine the amount of the fine particles S in the exhaust gas EG more accurately based on the signal current Is. It is also possible to achieve easy supply of the ions CP and air AR into the mixing space MX as the ion/gas ejection unit 11 combines the function of the ion source unit with the function of the gas ejection unit.

In the present embodiment, the air supply pipe 163 (gas flow passage 163H) is incorporated in the cable 160 so that the compressed air AR is supplied from the transfer pump 300 to the ion/gas ejection unit 11 through the air supply pipe 163 (gas flow passage 163H). There is no need to provide, at a position adjacent to the fine particle sensor 10, a pump for ejecting the compressed air AR to the ion/gas ejection unit 11. There is also no need to provide and arrange an air supply tube or pipe separately from the cable 160. It is thus possible to achieve easy supply of the compressed air AR to the ion/gas ejection unit 11 as well as easy line arrangement for supply of the compressed air AR to the ion/gas ejection unit 11. As the air supply pipe 163 (gas flow passage 163H) is preferably incorporated inside the inner shield line 165 of the cable 160, it is possible to bring the air supply pipe 163 (gas flow passage 163H) into gas communication with the ion/gas ejection unit 11 more easily and assuredly.

The entire contents of Japanese Patent Application No. 2011-088549 (filed on Apr. 12, 2011) are herein incorporated by reference.

Although the present invention has been described above with reference to the specific exemplary embodiment, the present invention is not limited to the above-described exemplary embodiment. Various modifications and variations of the embodiment described above will occur to those skilled in the art in light of the above teachings.

Although the second floating potential PV2 is a positive potential having an effective potential value higher than that the first floating potential PV1 in the above embodiment, the second floating potential PV2 may alternatively be a negative potential having an effective potential value higher than that of the first floating potential PV1. Further, it suffices that the third floating potential PV3 is different from the first and second floating potentials PV1 and PV2 as long as the third floating potential PV3 has an effective potential value at which the auxiliary electrode 53 can exert a repulsive force on the stray ions CPF.

In the fine particle sensor 10, the aerial discharge is generated between the first and second electrodes. Although the first electrode and the second electrodes are opposed to and face each other in the above embodiment, the first and second electrodes may alternatively be located adjacent to each other so that the aerial discharge occurs in the form of a creeping discharge between these first and second electrodes.

Although the ion source unit and the gas ejection unit are combined into one as the ion/gas election unit 11 in the above embodiment, the ion source unit and the gas ejection unit may be provided separately in the fine particle sensor 10.

The transfer pump 300 may alternatively be adapted to compress and discharge any gas other than the air, such as nitrogen or oxygen, as the high-pressure gas.

Further, the gas ejection unit may have a pump to compress gas (air, nitrogen, oxygen etc.) and eject the compressed gas to the particle charging unit 12 although the transfer pump 300 is provided separately the ion/gas ejection unit 11 so that the compressed air AR is fed from the transfer pump 300 to the ion/gas ejection unit 11 and then ejected from the ion/gas ejection unit 11 to the particle charging unit 12 in the above embodiment.

In the above embodiment, each of the inner shield line 165 and the outer shield line 167 is formed from a braided wire of copper. The shield line 165, 167 may alternatively be formed by using a braided wire of aluminum etc. in place of the copper braided wire, or by winding a metal tape of copper, aluminum etc. around the coating layer 164d, 166. It is also alternatively feasible to form the shield line 165, 167 by, after placing a braided wire of copper, aluminum etc., winding a metal tape of copper, aluminum etc. around the braided wire. Further, the whole or part of the shield line 165, 167 may alternatively be formed from a metal pipe such as copper pipe or aluminum pipe.

As the isolation transformer 270, there can alternatively be used an ordinary isolation transformer in which primary and secondary coils are wound around a single common core. In this case, it is preferable to set the core to the first floating potential PV1.

It is feasible to provide and dedicate two separate isolation transformers to the ion-source power supply circuit 210 and the auxiliary-electrode power supply circuit 240, respectively, although the isolation transformer 270 is shared between the ion-source power supply circuit 210 and the auxiliary-electrode power supply circuit 240 in the above embodiment.

In the above embodiment, the constant-current supply circuit is used as the ion-source power supply circuit 210 as mentioned above. There can alternatively be used, as the ion-source power supply circuit 210, a direct-current constant current power supply in which the second output terminal is always set to a positive potential with respect to the first output terminal so as to maintain the effective value of the output current at a constant value, or a direct-current constant current power supply in which the second output terminal is set to a positive potential intermittently (in a half-wave rectification form or rectangular pulse form) with respect to the first output terminal so as to maintain the effective value of the output current at a so-called pulsating constant value.

The scope of the invention is defined with reference to the following claims.

What is claimed is:

1. A fine particle detection system for detecting the amount of fine particles in exhaust gas flowing through a metallic exhaust pipe, comprising: a fine particle sensor mounted to the exhaust pipe; a lead extending from the fine particle sensor; and a sensor drive control device connected to the lead, the fine particle sensor comprising: an ion source unit; a particle charging unit; an inner sensor casing; and an outer sensor casing, the ion source unit having: a first electrode set to a first floating potential; and a second electrode set to a second floating potential that is a positive or negative potential having an effective potential value higher than of the first floating potential, to generate ions by aerial discharge between the first and second electrodes, the particle charging unit having: a gas inlet hole for introducing the exhaust gas from the exhaust pipe; a mixing space for mixing the introduced exhaust gas with the ions generated from the ion source unit so as to form charged fine particles by charging the fine particles in the introduced exhaust gas with some of the ions; a gas outlet hole for discharging the introduced exhaust gas together with the charged fine particles to the exhaust pipe; and a trapping electrode being electrically continuous with the first electrode and adapted to trap a remainder of the ions that remain as stray ions without being used for charging of the fine particles, the inner sensor casing being electrically continuous with the first electrode and the particle charging unit, while being electrically insulated from the second electrode and the exhaust pipe, and located at a position nearer to the lead than the ion source unit and the particle charging unit so as to circumferentially surround the second electrode, the outer sensor casing being electrically continuous with the exhaust pipe and thereby set to a ground potential, while being electrically insulated from the second electrode, the particle charging unit and the inner sensor casing, and located so as to circumferentially surround and electromagnetically shield parts of the ion source unit, the particle charging unit and the inner sensor casing located outside the exhaust pipe, the lead being a double-shield cable having: a power supply wiring line connected to the second electrode; an inner shield line being electrically continuous with the inner sensor casing, while being electrically insulated from the power supply wiring line, and circumferentially surrounding the power supply wiring line; and an outer shield line being electrically continuous with the outer sensor casing, while being electrically insulated from the inner shield line, and circumferentially surrounding and electromagnetically shield the inner shield line, the sensor drive control device comprising: an ion-source power supply circuit; a signal current detection circuit; an inner circuit casing; and an outer circuit casing, the ion-source power supply circuit having: a first output terminal set to the first floating potential and being electrically continuous with the first electrode of the ion source unit through the inner shield line; and a second output terminal being electrically continuous with the second electrode of the ion source unit through the power supply wiring line, and adapted to output a predetermined constant current through the second output terminal, the current signal detection circuit having: a signal input terminal connected to the first output terminal of the ion-source power supply circuit; and a ground input terminal connected to the ground potential, to detect a signal current flowing between the first output terminal of the ion-source power supply circuit and the ground potential, the inner circuit casing being electrically continuous with the first output terminal of the ion-source power supply circuit and surrounding the ion-source power supply circuit, the outer circuit casing connected to the ground potential and surrounding and electromagnetically shielding the ion-source power supply circuit, the inner circuit casing and the current signal detection circuit.

2. The fine particle detection system according to claim 1, wherein the sensor drive control device further comprises an isolation transformer through which the ion-source power supply circuit is externally supplied with power; and wherein the outer circuit casing surrounds and electromagnetically shields the isolation transformer.

3. The fine particle detection system according to claim 1, wherein the particle charging unit has an auxiliary electrode set to a third floating potential being different from the first and second floating potentials and having an effective potential value at which a repulsive force is exerted on the stray ions so as to assist in the trapping of the stray ions by the trapping electrode, while being electrically insulated from the first and second electrodes, wherein the inner sensor casing circumferentially surrounds the auxiliary electrode, wherein the double-shield cable has an auxiliary wiring line being electrically continuous with the auxiliary electrode;

wherein the sensor drive control device further comprises an auxiliary-electrode power supply circuit having: a first output terminal set to the first floating potential and being electrically continuous with the first output terminal of the ion-source power supply circuit; and a second output terminal set to the third floating potential and being electrically continuous with the auxiliary electrode through the auxiliary wiring line; and wherein the inner circuit casing surrounds the auxiliary-electrode power supply circuit.

4. The fine particle detection system according to claim 3, wherein the sensor drive control device further comprises an isolation transformer through which the auxiliary-electrode power supply circuit is externally supplied with power; and wherein the outer circuit casing surrounds and electromagnetically shields the isolation transformer.

5. The fine particle detection system according to claim 1, wherein the fine particle sensor comprises a gas ejection unit to eject a gas into the mixing space of the particle charging unit; and wherein the particle charging unit introduces the exhaust gas by suction into the mixing space through the gas inlet hole upon ejection of the gas from the gas ejection unit so that the introduced exhaust gas and the ejected gas are mixed together in the mixing space of the particle charging unit and discharged to the exhaust pipe through the gas outlet hole.

6. The fine particle detection system according to claim 5, wherein the ion source unit and the gas ejection unit are combined into one unit so that the ions and the gas are ejected together into the mixing space of the particle charging unit.

7. The fine particle detection system according to claim 5, wherein the double-shield cable includes a gas flow passage in communication with the gas ejection unit so as to supply the gas to the gas ejection unit through the gas flow passage.

8. The fine particle detection system according to claim 1, wherein the second floating potential is a positive potential higher than the first floating potential;

wherein the second electrode has a needle-like pointed end portion;

wherein the first electrode has a surface facing and spaced apart from the needle-like pointed end portion of the second electrode; and wherein the ion source unit is adapted to generate, as the aerial discharge, positive needle corona discharge around the needle-like pointed end portion of the second electrode in a space between the first and second electrodes.

* * * * *